US008547095B2

(12) United States Patent
Budker et al.

(10) Patent No.: US 8,547,095 B2
(45) Date of Patent: Oct. 1, 2013

(54) DETECTION OF MAGNETIC RESONANCE SIGNALS USING A MAGNETORESISTIVE SENSOR

(75) Inventors: Dmitry Budker, El Cerrito, CA (US); Alexander Pines, Berkeley, CA (US); Shoujun Xu, Houston, TX (US); Christian Hilty, College Station, TX (US); Micah P. Ledbetter, Oakland, CA (US); Louis S. Bouchard, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 704 days.

(21) Appl. No.: 12/753,306

(22) Filed: Apr. 2, 2010

(65) Prior Publication Data

US 2010/0264917 A1  Oct. 21, 2010

Related U.S. Application Data

(63) Continuation-in-part of application No. PCT/US2008/078820, filed on Oct. 3, 2008.

(60) Provisional application No. 60/977,698, filed on Oct. 5, 2007.

(51) Int. Cl.
 *G01V 3/00* (2006.01)
(52) U.S. Cl.
 USPC .......................................... 324/307; 324/309
(58) Field of Classification Search
 USPC ......... 234/300–322; 210/695, 746; 204/556; 324/300–322, 252; 600/407–445
 See application file for complete search history.

(56) References Cited

U.S. PATENT DOCUMENTS

| 6,046,587 | A | 4/2000 | King et al. |
| 7,179,383 | B1* | 2/2007 | Porter et al. .................. 210/695 |
| 7,573,264 | B2* | 8/2009 | Xu et al. ....................... 324/304 |
| 7,994,783 | B2* | 8/2011 | Ledbetter et al. ............. 324/306 |
| 2011/0001478 | A1* | 1/2011 | Wemmer et al. .............. 324/309 |

OTHER PUBLICATIONS

Verpillat et al., "Remote detection of nuclear magnetic resonance with an anisotropic magnetoresistive sensor," Proceedings of the National Academy of Sciences, vol. 105, No. 7, pp. 2271-2273, (Feb. 19, 2008).
Anwar et al., "Spin Coherence Transfer in Chemical Transformations Monitored by Remote Detection NMR, " Analytical Chemistry, vol. 79, No. 7, pp. 2806-2811, (Apr. 1, 2007).
Ferreira et al, "Tuning of MgO barrier magnetic tunnel junction bias current for picotesia magnetic field detection," Journal of Applied Physics, vol. 99, pp. 08K706-1-08K706-3, (Apr. 27, 2006).

(Continued)

*Primary Examiner* — Brij Shrivastav
(74) *Attorney, Agent, or Firm* — Lawrence Berkeley National Laboratory

(57) ABSTRACT

A method and apparatus are described wherein a micro sample of a fluidic material may be assayed without sample contamination using NMR techniques, in combination with magnetoresistive sensors. The fluidic material to be assayed is first subject to pre-polarization, in one embodiment, by passage through a magnetic field. The magnetization of the fluidic material is then subject to an encoding process, in one embodiment an rf-induced inversion by passage through an adiabatic fast-passage module. Thereafter, the changes in magnetization are detected by a pair of solid-state magnetoresistive sensors arranged in gradiometer mode. Miniaturization is afforded by the close spacing of the various modules.

21 Claims, 4 Drawing Sheets

(56) References Cited

OTHER PUBLICATIONS

Freitas et al., "Magnetoresistive sen,ors," Journal of Physics: Condensed Matter, vol. 19, pp. 1-21 (Feb. 9, 2007).
Gomez et al., "A method to design high SNR nanoscale magnetic sensors using an array of tunnelling magneto-resistance (TMR) devices," Journal of Physics D: Applied Physics, vol. 40, pp. 4396-4404, (2007).
Kominis et al., "A subfemtotesla multichannel atomic magnetometer," Nature, vol. 422, pp. 596-599, (Apr. 10, 2003).
Ledbetter et al., "Zero-field remote detection of NMR with a microfabricated atomic magnetometer," Proceedings of the National Academy of Sciences, vol. 105, No. 7, pp. 2286-2290, (Feb. 19, 2008).
Minard et al., "Communications Picoliter 1H NMR Spectroscopy," Journal of Magnetic Resonance, vol. 154, pp. 336-343, (Jan. 14, 2002).
Mioule et al., "Amplification of xenon NMR and MRI byremote detection," Proceedings of the National Academy of Sciences, vol., 100, No. 16, pp. 9122-9127, (Aug. 5, 2003).
Olson et al., "High-Resolution Microcoil 1H-NMR for Mass-Limited, Nanoliter-Volume Samples," Science, vol. 270, pp. 1967-1970, (Dec. 22, 1995).
Pannetier et al., "Femtotesla Magnetic Field Measurement with Magnetoresistive Sensors," Science, vol. 304, pp. 1648-1650, (Jun. 11, 2004).
Pannetier-Lecoeur et al., "RF Response of Superconducting-GMR Mixed Sensors, Application to NQR," IEEE Transcations on Applied Superconductivity, vol. 17, No. 2, pp. 598-601, (Jun. 2007).
Pekas et al., "Giant magnetoresistance monitoring of magnetic picodroplets in an integrated microfluidic system," Applied Physics Letters, vol. 85, No. 20, pp. 4783-4785, (Nov. 15, 2004).
Verpillat et al., "Remote detection of nuclear magnetic resonance with an anisotropic magnetoresistive sensors," Proceedings of the National Academy of Sciences, vol. 105, No. 7, pp. 2271-2271, (Feb. 19, 2008).
Webb, "Nuclear magnetic resonance of mass-limited samples using small RF coils," Analytical and Bioanalytical Chemistry, vol. 388, pp. 525-528, (Mar. 6, 2007).
Wong-Foy et al., "Laser-polarized 129Xe NMR and MRI at Ultralow Magnetic Fields," Journal of Magnetic Resonance, vol. 157, pp. 235-241, (2002).
Wood et al., "Submicron giant magnetoresistive sensors for biological applications," Sensors and Actuators A, vol. 120, pp. 1-6, (2005).
Xu et al., "Magnetic resonance imaging with an optical atomic magnetometer," Proceedings of the National Academy of Sciences, vol. 103, No. 34, pp. 12668-12671, (Aug. 22, 2006).
International Search Report and Written Opinion for International Application No. PCT/US08/78820 mailed Dec. 11, 20089.

* cited by examiner

DETECTION OF MAGNETIC RESONANCE SIGNALS USING A MAGNETORESISTIVE SENSOR

CROSS REFERENCE TO RELATED APPLICATIONS

This utility patent application is a continuation in part of and claims the benefit of priority to International PCT Application PCT/US2008/078820, filed Oct. 3, 2008, which in turn claims priority to our earlier filed U.S. Provisional Application Ser. No. 60/977,698, filed Oct. 5, 2007, both of which applications are hereby incorporated by reference as if fully set forth in their entirety.

STATEMENT OF GOVERNMENTAL SUPPORT

The invention described and claimed herein was made in part utilizing funds supplied by the U.S. Department of Energy under Contracts No. DE-AC03-76SF00098, and DE-AC02-05CH11231 with the Regents of the University of California for the management and operation of the Lawrence Berkeley National Laboratory. The government has certain rights in this invention.

BACKGROUND OF THE INVENTION

1. Field of the Invention

This invention relates generally to the assay of microliter amounts of a fluidic sample using magnetic resonance, and more particularly to nuclear magnetic resonance (NMR) imaging methods and apparatus incorporating magnetoresistive sensors for the conduct of such assays.

2. Background of the Invention

Miniaturized fluid handling devices have recently attracted considerable interest in many areas of science. Such microfluidic chips perform a variety of functions, ranging from analysis of biological macromolecules to catalysis of reactions and sensing of fluids in the liquid or gas phase. Some microfluidic chips also enable assay of combined multiphase reactions (solid-liquid-gas).

Currently, most microfluidic flow measurements rely on optical detection of markers, requiring the injection of tracers and use of transparent devices. These techniques, however, by their very nature result in a degree of sample contamination due to the addition of the marker. Moreover, optical methods may not be applicable for chips or where the fluidic sample is optically opaque. Another drawback of these techniques is their lack of specificity, where one seeks to differentiate between different chemical species in a fluidic sample, or, more generally, where one seeks to track two or more species together, given the limitations of a marker. Suggested approaches which do not require the use of injected markers include the use of superconducting quantum interference devices (SQUIDs) and the use of alkali-vapor atomic magnetometers. However these devices require cryogenics in the case of the former, or heated vapor cells in the case of the latter. For microfluidic measurements, there thus remains a need for a detection system which does not have these drawbacks, is compact and relatively inexpensive.

BRIEF DESCRIPTION OF THE INVENTION

By way of this invention, it has been found that solid state magnetoresistive sensors, including anisotropic magnetoresistive (AMR) sensors, giant magnetoresistive (GMR) anisotropic magnetoresistive sensors, and magnetic tunnel junction (MTJ) sensors can afford the high sensitivities needed for use with NMR remote detection modalities to profile microfluidic flow and assay very small amounts of a substance. As used herein, microfluidic flow is used to denote capillary flow through tubes of anywhere from 1 mm diameter down to about 100 nm in diameter. Sample sizes are typically in the nanoliter range. Through transient measurements of changes in magnetic field, anisotropic magnetoresistive sensors for NMR are well adapted for non-invasive, yet sensitive determination of the flow field and provide a potentially powerful tool to profile flow in capillaries and miniaturized flow devices, as well as for NMR imaging and spectroscopic analysis.

In an embodiment of this invention, the encoding of NMR information is separated from the detection function. First, a fluidic sample to be assayed (for example, water) is prepolarized. That is, the nuclear spin of the protons is preferentially oriented, in one embodiment, collinear to the direction of an applied magnetic field of a suitably strong magnet. It is this induced excess proton spin in the direction of the field that creates a small net magnetization of the material. To enable measurement of flow, the thus polarized fluidic sample is encoded by passing it in an embodiment through an adiabatic fast passage (AFP) module where the polarity of the fluid is repeatedly flipped (that is inverted) 180 degrees in a gradient field which steadily changes (either decreasing or increasing) in the direction of flow. The thus inverted fluid passes to a detection zone, where it is monitored as its passes through the zone. Generally, the static field at the detector is typically much smaller than the prepolarization field, by one to several orders of magnitude. The magnetoresistive sensors of the detection zone are positioned in close proximity to the microchannel carrying the sample. By knowing the diameter of the microfluidic channel, the timing of the on/off cycle of the AFP module, and by downstream recording of the magnetic field peaks, time of flight and thus fluid flow rates may be determined.

In another embodiment of the invention, the flow of fluid can be temporarily stopped, or its velocity altered. By stopping or varying flow velocity, the spin relaxation time $T_1$ of a sample can be measured, and thus the nature of the fluidic sample determined.

It should be appreciated that this type of experiment is not limited to $T_1$ encoding and that other types of NMR encoding can be performed, such as encoding based on chemical shift (between different nuclei), chemical shift differences (homonuclear), velocity, $T_2$ relaxation time or even diffusion weighting. The encoding region can be optimized to perform almost any type of NMR measurement.

It should also be appreciated that the "magnetization" of the polarized fluid decreases over time as the net orientation of induced spins relaxes with time, the spins tending to return to a more random state. In fact, within a few seconds relaxation can occur to such a degree that the ability to detect changes in the magnetic field of the fluid by GMR sensors significantly degrades. Thus, it is desirable to bring the three functions (pre-polarization, encoding and detection) together, in such a way that the flow path is shortened as much as possible, thus reducing the time lapse between polarization and detection. Accordingly, the greater the miniaturization of the system, the more sensitive it will be to changes in nuclear magnetization.

BRIEF DESCRIPTION OF THE DRAWINGS

The foregoing aspects and others will be readily appreciated by the skilled artisan from the following detailed description and illustrative embodiments when read in conjunction with the accompanying drawings. It is to be noted that the appended drawings illustrate only typical embodiments of this invention and are therefore not to be considered limiting of its scope, for the invention may admit to other equally effective embodiments.

DETAILED DESCRIPTION OF THE INVENTION

The methods and apparatus of this invention use solid-state magnetoresistive sensors to detect changes in the magnetic field of a material after is has been magnetized. By using such solid-state detectors, one can obtain accurate fluidic measurements for very small amounts of fluids in the micro sample (nanoliter) range without contamination of the sample. In this context it has been found that the use of magnetoresistive sensors, including both anisotropic magnetoresistive (AMR) sensors, especially those that rely upon the giant magnetoresistive (GMR) effect, and magnetic tunnel junction (MTJ) sensors, though compact and relatively cheap, have sufficient sensitivity to be useful in the detection of small changes in the magnetic field of these small samples.

As used herein, the term magnetoresistance is the property of a material to change the value of its electrical resistance in the presence of an external magnetic field. The term anisotropic magnetoresistance (AMR) is used to denote a property of a material such as a thin strip of ferrous material wherein a change in resistance of the material occurs when a magnetic field is applied perpendicular to the direction of current flow, and includes both AMR and GMR sensors. In the case of GMR sensors, which have alternating ferromagnetic and non-magnetic metal layers, this effect is most pronounced.

The exact construction and operation of magnetoresistive sensors does not form a part of this invention, and various constructions may be used. A good description as to the operation of such devices, for example, can be found in publicly available information such as that posted on Honeywell Corporation's web site, which includes descriptions of their magnetic sensor product offerings. Typically, these sensing elements are made of metal films deposited onto a silicon substrate to form a Wheatstone resistor bridge, with each of four metal strips acting as a resistor. Powered up, a bridge voltage supply causes current to flow through each resistor. In detection mode, the presence of an applied transverse magnetic field causes the magnetization in two of the oppositely placed resistors to rotate towards the current, resulting in a change in resistance. It is this resistance change which is measured and is indicative of changes in the localized magnetic field. In this manner, when an AMR sensor is placed in close proximity to a capillary channel transporting a prepolarized fluidic sample which has been subject to encoding by, for example, AFP spin-flip, transient changes in the magnetic field strength can be detected and displayed.

Figure 1:
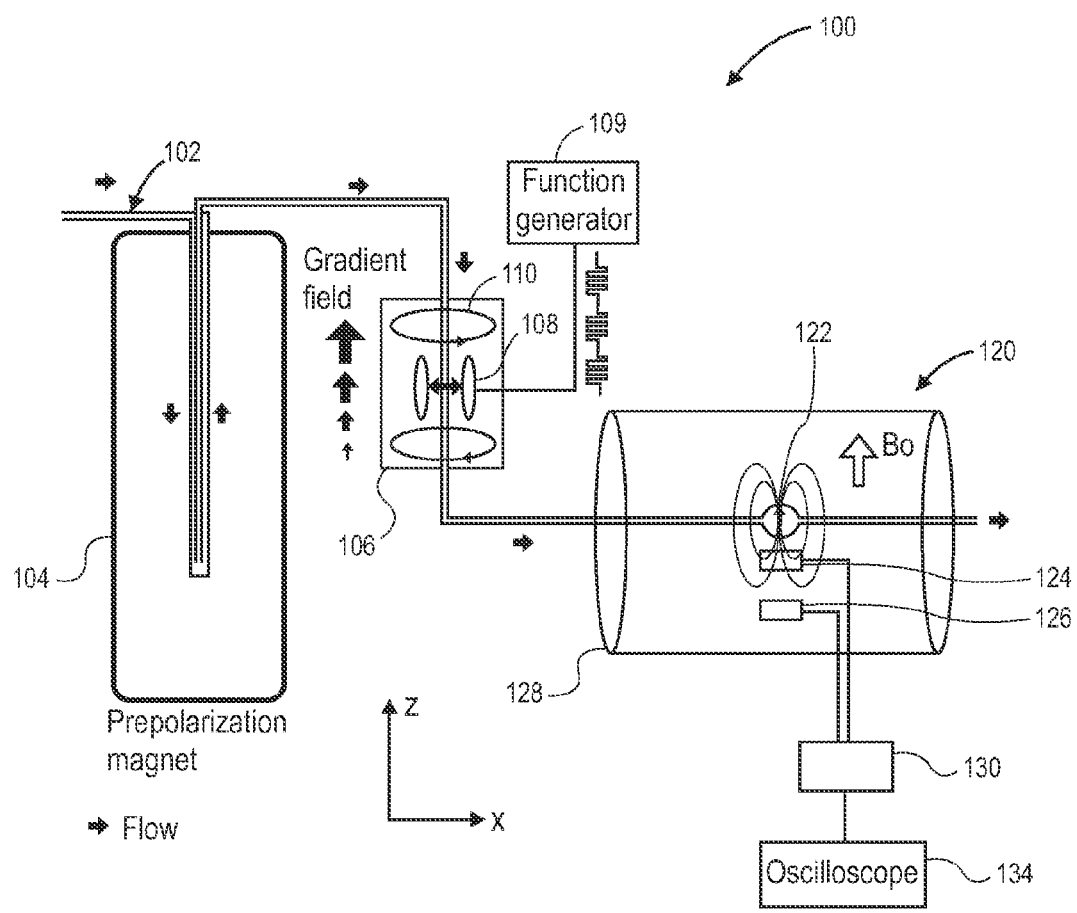
FIG. 1 is a schematic diagram showing the arrangement of the various modules employed in the assay of this invention, in connection with the Experiment later discussed.

With reference now to FIG. 1, the component arrangement used in the Experiment described in the next section is illustrated. Here, a survey apparatus 100 includes a polarization magnet module 104, an AFP module 106, and a sensing module 120, capillary tube 102 providing a pathway for transporting the fluidic sample to be assayed from one module to another. Module 104 provides the magnetic field (which need not be homogeneous) used to polarize the fluid, a necessary first step in the NMR/MRI imaging process. In this step, the spin of the atomic nuclei become more organized, creating a magnetic field within the fluid, the changes to which may later be detected. The magnet of module 104 may either be a permanent magnet, superconducting magnet, or one that is switchable, such as an electromagnet. The stronger the applied magnetic field, the stronger will be the ultimately measured signal, the increase in strength being in linear proportion. To further enhance the strength of the later detected signal, residence time in the pre-polarizing magnetic field is selected to be at least several times the anticipated relaxation times $T_1$ of the fluidic samples being surveyed. One of ordinary skill in the art will appreciate that other, preferably non-contaminating, methods may be used to pre-polarize the fluidic sample. By way of illustration, such methods could include spin-exchange optical pumping of noble gases such as Xe-129 and He-3, metastability-exchange optical pumping with He-3, etc.

Capillary tube 102 transports the polarized fluidic sample to the next station, AFP module 106 in which the sample is encoded. Here, radio frequency (rf) radiation is applied to the sample at the appropriate frequency to produce spin flips. The protons of the fluid are thus flipped from an orientation parallel to the original magnetic field to a higher energy state, anti-parallel to the field or vice versa. The general operating principles of AFP modules, though well known and not a part of this invention are now briefly reviewed. In AFP module 106, an alternating magnetic field is applied to the fluid by means of rf coils 108, which are driven by function generator unit 109, the unit generating sinusoidal rf waves, which in turn create the required alternating magnetic fields. The required radio frequency can be adjusted by changing the value of the magnetic field in the AFP device. In experiments to date, frequencies in the kilohertz range have been used, so that the static field in the AFP region is commensurate with the Earth's magnetic field of about 50 microtesla. In order to effectuate inversion of NMR spin, in one embodiment, the rf frequency may be varied over a given range so that eventually it matches the Larmor resonant frequency of the fluidic sample, at which point inversion occurs. Alternatively, if the frequency of the if signal is kept constant, the same effect can be achieved by varying the strength of the magnetic field along the direction of flow, such as by the use of gradient coils 110 as illustrated. Here, in the embodiment shown, the gradient field decreases in the direction of flow, the point of Larmor frequency resonance occurring near the midpoint between the coils.

The now encoded fluid is next transported to sensing module 120, the sensor detection area surrounded by magnetic shield 128. The shield, which can be single or multilayered, is constructed out of a high-permeability magnetically soft alloy such as Mumetal®, CO-NETIC® [both products sold commercially by Magnetic Shield Corporation, Bensenville, Ill.], or permalloy. Information regarding commercially available materials and examples of shielding design are available, among many other places, at the web page of Amuneal, Inc.: http://www.amuneal.com/pages/magshield.php.

It is to be appreciated that although a shield was used in the Experiment, its use is not critical to the invention. In some situations its use may be avoided entirely by the use of multiple sensors arranged in gradiometer mode so as to allow for the subtraction out of ambient field fluctuations.

Figure 2:
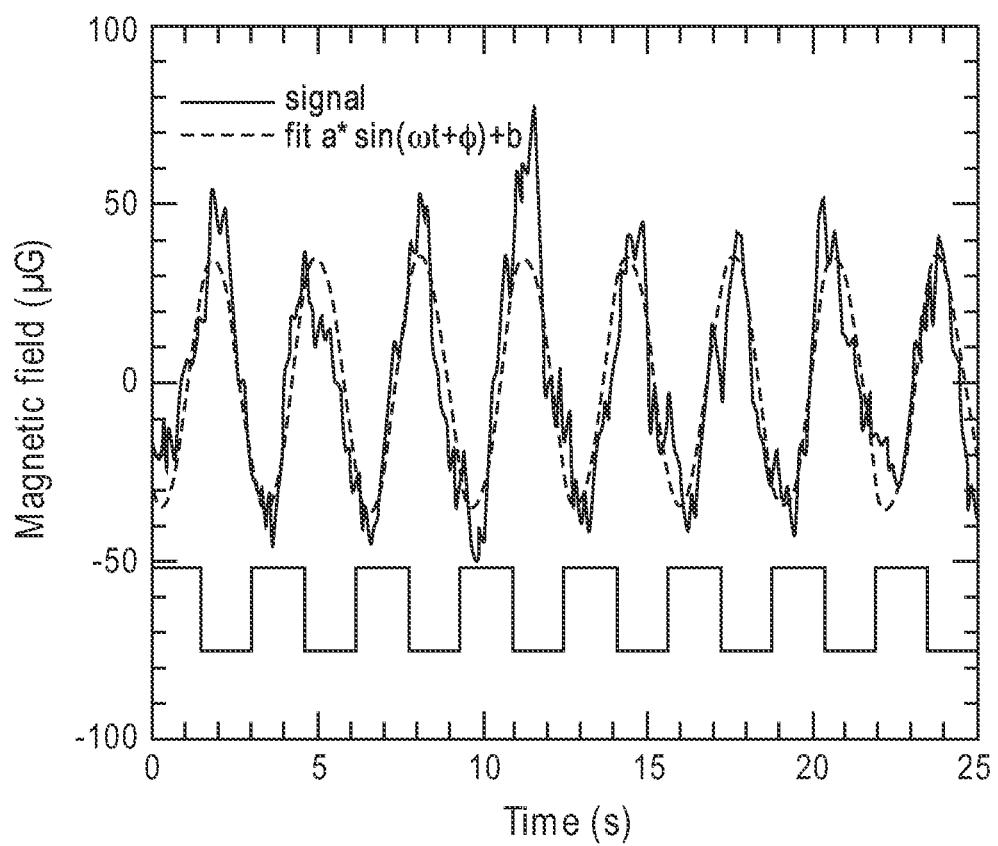
FIG. 2 is a trace of the results of the Experiment for magnetic fields detected with a 0.3-Hz modulation frequency (modulation of the AFP's delay between successive inversions), plotted against the on-off pattern of the adiabatic magnetic-field inverter.

The sensing module includes a sensor station, which in FIG. 1 comprises enlarged sampling area (glass ball) 122. The use of an enlarged sampling area increases the amount of sample material at the point of imaging. The greater amount of sample in turn makes detection of changes in magnetic field easier, and thus helps improve overall sensitivity of the unit. It is to be appreciated that provision for an enlarged area at the point of detection is not required, with other approaches such as matching the size of the sample channel to the detector size and minimizing magnetization loss due to excess distance between the channel and the detector can be used to achieve essentially the same effect The AMR sensors as shown in the FIG. 1 are arranged in gradiometer mode, the first sensor 124 used to detect changes in the magnetic fields associated with the flowing fluid, the second sensor 126 spatially removed from the sample and used to measure the ambient magnetic field. Electronic module 130, which could be analog or digital (such as among other options an analog differential amplifier, a computer, or the like), receives the measurements from both sensors and subtracts the reading of sensor 126 from the reading of sensor 124 in order to eliminate the contribution of detected background. The results of the readings from electronic module 130 can then be displayed on an oscilloscope 134, the gain of the display adjusted to best observe changes in the detected magnetic field. Such a detected result is illustrated in FIG. 2.

It is to be noted that if the relaxation time $T_1$ of the sample is to be determined as part of a general assay using NMR imaging techniques, the AFP unit can be switched off. In this mode, the fluid sample passes through the AFP unit with its spin orientation unchanged prior to reaching sensing module 120.

In an embodiment of the invention, AFP inversion can be replaced by a non-adiabatic inversion. It can also be replaced by an excitation pulse (other than 180 degrees flip), and possibly followed by MRI imaging gradients, or some other form of encoding normally used in NMR/MRI experiments. For example, a series of two 90 degree pulses could be used to phase encode a free induction decay signal. This could then provide information about J-couplings or chemical shifts. It is also possible to make any of these inversion or excitation pulses selective of the nuclear species, if more than one nuclear species is present in the sample under study. In low magnetic fields, heteronuclear systems provide a convenient way to perform selective labeling experiments, where only a nucleus of interest is tagged. This tagging permits the study of chemical transformations. Selective labeling can also be done on the same nucleus if the incoming fluids originate from several different channels and the spins in each channel are tipped differently. Following the possible mixing of the different incoming channels, this would enable, for example, the identification of the various fluids.

EXPERIMENT

The experiment was set up as shown in FIG. 1. Tap water, pre-polarized by flowing it through a Bruker 17 Tesla magnet, flows through an adiabatic-inversion region, where its polarization is periodically reversed, and is flowed past an anisotropic magneto resistive (AMR) detector. The adiabatic polarization inverter incorporates a set of coils in anti-Helmholtz configuration to supply a gradient of $B_z$. A second set of Helmoltz coils is used to apply a 5.5 KHz oscillating field in the x direction, resonant with the proton's Larmor frequency in the center of the inverter. When the oscillating field is on, as the water flows through the device, its magnetization is adiabatically reversed. Switching the oscillating field on and off results in magnetization either parallel or anti-parallel to the bias field.

After the adiabatic inverter, the water flows to the detection region consisting of a 0.5-$cm^3$ glass ball adjacent to a pair of Honeywell HMC 2003 hybrid 3-axis AMR sensors arranged in gradiometer mode in order to cancel out common-mode magnetic field noise. The Honeywell HMC 2003 hybrid 3-axis sensor comprises an HMC1001 AMR single axis sensor and an HMC 1002 two-axis sensor mounted to a single printed-circuit board. (See http://www.ssec.honeywell.com/magnetic/products.html) The active part of each sensor is a thin film with an area of about 1.5 mm×1.5 mm packaged in a chip with dimensions of 10 mm×3.9 mm×1.5 mm. The detection region was housed inside a single layer of magnetic shielding with open ends. The water carrying tube was 1/16 inch internal diameter, and the flow rate was 3.8 $cm^3$ per second, corresponding to an average speed of water of approximately 2 meters per second. The average travel time from the magnet to the inverter was about 1.5 seconds and about 0.5 seconds from the inverter to the detector.

Data were recorded on a digital oscilloscope averaging for about 20 minutes for modulation frequencies in the range of 0.3 Hz to 1.7 Hz. The resulting signal for a modulation frequency of 0.3 Hz is shown in FIG. 2. Neglecting fluid mixing in the transfer tube and detection ball, one would expect that the signal should be a square wave for low modulation frequencies. However, considerable mixing produced signals well approximated by a sinusoid, as indicated by the dashed line in FIG. 2.

Figure 3:
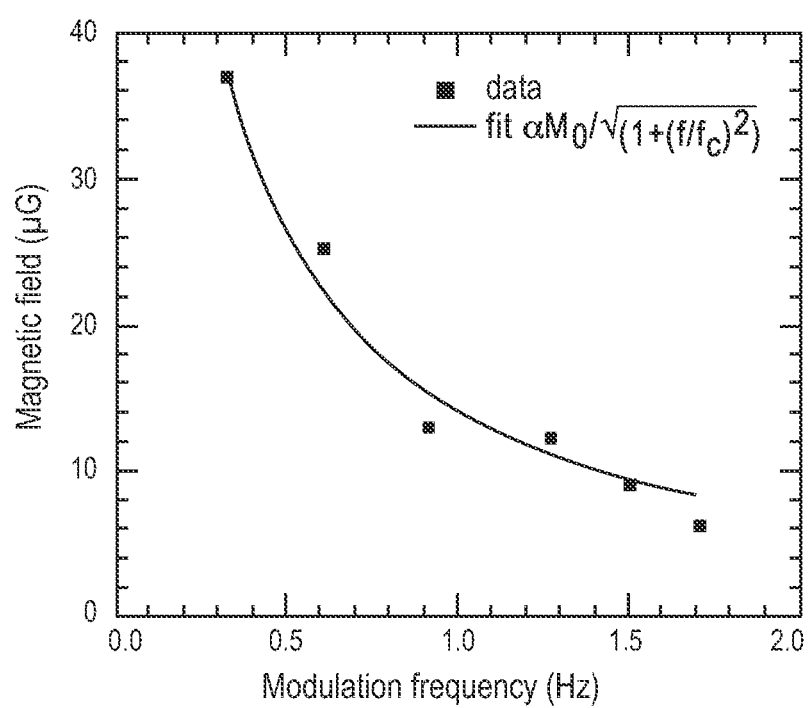
FIG. 3 is a graph of magnetic field vs. modulation frequency, and plots the amplitude of the modulated water signal obtained in the Experiment, fitted to an RC filter transfer function.

All the data were fit to sinusoidal profiles and the resulting amplitudes are shown as a function of frequency in FIG. 3. The rapid drop in amplitude is due to mixing of the magnetization as it propagates from the AFP device through the detection ball, effectively integrating the magnetization for some time. Simple models for the spectral response of the system can be obtained in analogy to a low-pass RC filter where the frequency dependence of the signal is $S_0 = \alpha M_0 / \sqrt{1+(f/f_c)^2}$. Here, $\alpha$ is a proportionally constant dependent on geometry, relating the magnetic field at the sensor to the magnetization of the sample and $f_c$ is a cutoff frequency. Overlaying the data in FIG. 3 is a fit to this model function with $\alpha M_0 = 67$ μG and $f_c = 0.2$ Hz.

Figure 4:
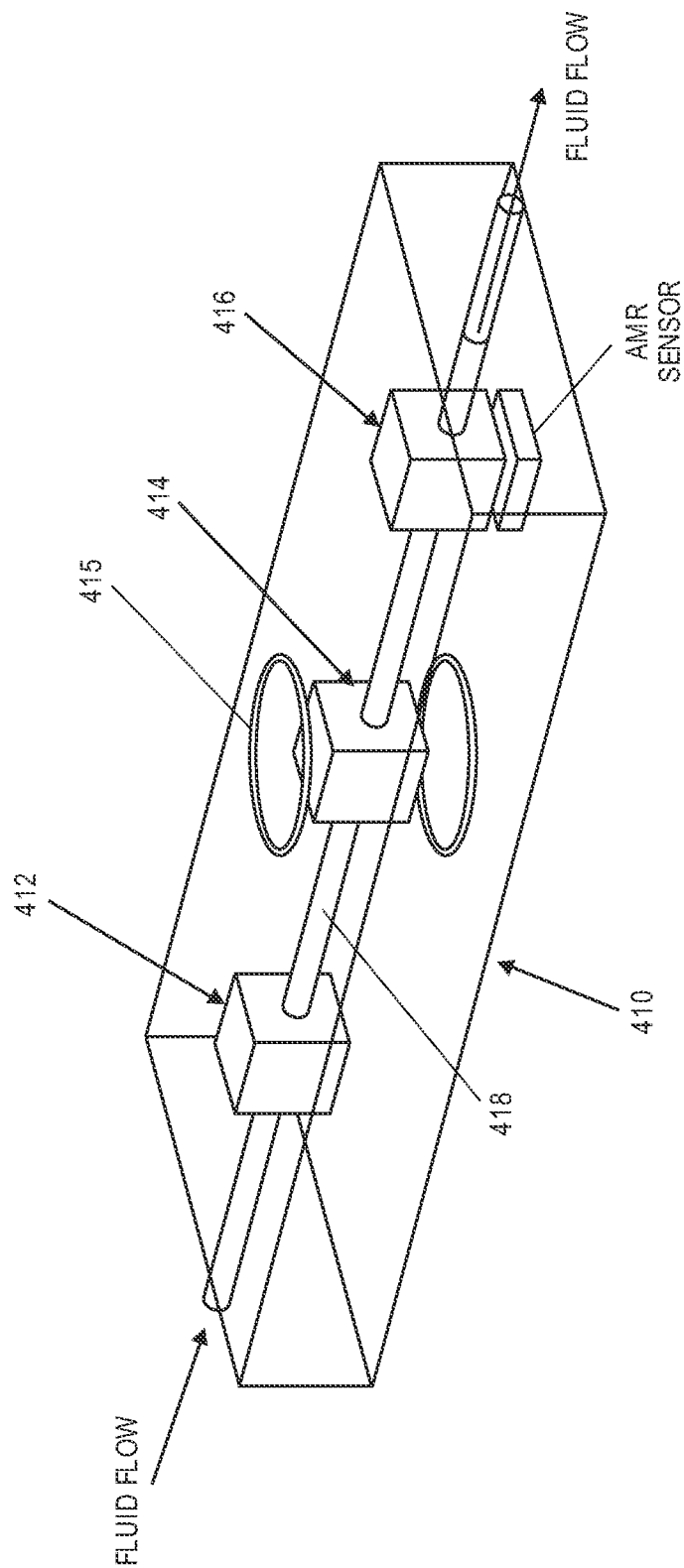
FIG. 4 is a schematic depiction of an apparatus according to an embodiment of this invention in which the various modules are embodied in a single platform, such as a printed circuit board or a chip of glass or silicon.

It is to be appreciated that as path length from the pre polarization module to the magnetometer is reduced, the greater the magnetization of the sample will be at the point of measurement, and thus the more sensitive the detector will be to changes in the nuclear magnetization of the fluid. Concomitantly, the shorter the path, the smaller the magnets that are needed for polarization. In one embodiment, this distance can be reduced significantly by integrating all of the active components of the system onto a single platform, or base as shown in FIG. 4. The platform may be a printed circuit board, or a glass, or silicon supporting structure. In another embodiment incorporating further miniaturization, the components may be incorporated as part of a single chip. Particularly well suited for such single board or on-chip modes are the use of small, permanent magnets.

In such integrated embodiment, a base or substrate 410 is provided on which are incorporated a prepolarization unit 412, an encoding unit 414 (including gradient coils 415) and an AMR detection unit 416. Fluid is transported from one unit to the next through microfluidic channel 418. Magnetic shielding (not shown) may be provided to encase base 410, or more locally provided to encase the area immediately surrounding AMR detection unit 416. In this embodiment the microfluidic tube may be continuous, and the use of an expanded section at the point of detection can be eliminated, depending upon the sensitivity of the AMR sensors, especially in the case of anticipated improvements in giant magnetoresistive sensor materials, such that the sensitivity of these detectors is greatly enhanced.

While the invention has been described in connection with fluidic measurements, it is to be appreciated that methodology of this invention can be used for the detection of both gases and liquids, and as used herein, the term "fluid" should be understood to cover materials in either or both phases. Furthermore, the detection methods of the invention made be used in the assay of solids and semisolids, be they dissolved, suspended or embedded in a fluid, or flowable in neat or some other form. In addition, if several different nuclear species are found in the sample, it is also possible to selectively address a particular species. This provides a way to selectively label a desired nucleus in a compound when more than one compound is used, or if the compound is to undergo a chemical transformation.

Notwithstanding the fact that the various embodiments have been illustrated in connection with the use of AMR sensors in the context of NMR analysis, AMR sensors may also be used in connection with electron paramagnetic resonance (EPR) or electron spin resonance (ESR) analysis. This is possible given the analogy of the basic physical concepts of EPR to those of NMR, as both NMR and EPR are variations of magnetic resonance in general. In EPR, however, it is electron spins that are excited rather than those of atomic nuclei, and thus as most stable molecules have all their electrons paired, the EPR technique is less widely used than NMR. However, this same limitation also suggests the use of EPR can be of great specificity.

Though the invention has been described with respect to magnetoresistive sensors in general, including anisotropic magnetoresistive sensors, and giant magnetoresistive sensors, as previously noted, other types of sensors may be employed in the practice of the invention. By way of example, but without intending to be limited thereby, magnetic tunnel junction (MTJ) sensors (a form of magnetoresistive sensor), and similar solid-state sensors may be used to perform the detection function.

Also note that in experiment described above, the encoding region was placed in the magnetic field from the superconducting magnet, and corresponded to a Larmor precession frequency of 5.5 kHz. Other values of the magnetic field could be used, from near earth field (50 micro Tesla), to fields in the neighborhood of 1 Tesla (perhaps generated by a well shimmed permanent magnet), all the way up 10 Tesla (generated by superconducting magnets). Regarding the nature of the prepolarization magnetic field, though the field need not be homogeneous, strong (>1 Tesla) homogeneous fields (as was the case of the Example) may be required for chemical shift encoding, where the assay process is focused on the obtaining of precise sample chemical analysis. In cases not requiring homogeneous fields, however, simpler magnets may be used to provide the required prepolarization, the use of such simpler magnets further facilitating miniaturization.

As miniaturization continues to advance it is seen that the use of AMR detection will ultimately allow for the incorporation of this detection system with other device, facilitating construction of dedicated "lab on a chip" devices. Also, though the use of only one channel is illustrated in FIG. 4, such chips could be provided with multiple channels for the taking of simultaneous comparison readings, or the simultaneous assay of a plurality of fluid samples. With these improvements, room temperature, solid state devices can be used to provide an inexpensive and robust alternative to detection of NMR, without the need for cryogenics.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A device for detection of changes in a magnetization of a fluid sample including:
   a. a pre-polarization module configured to pre-polarize the fluid sample;
   b. an encoding module configured to encode the fluid sample by adiabatic fast passage;
   c. a detection module comprising at least one magnetoresistive sensor, the detection module configured to detect changes in the magnetization of the fluid sample, the pre-polarization, encoding, and detection modules being in proximity to each other; and
   d. a tube for transporting the fluid sample from the pre-polarization module to the encoding module to the detection module.

2. The device of claim 1 wherein the pre-polarization module includes one or more permanent, superconducting, or electro magnets.

3. The device of claim 1 wherein the magnetoresistive sensor is selected from the group consisting of an anisotropic magnetoresistive sensor, a giant magnetoresistive sensor, and a magnetic tunnel junction sensor.

4. The device of claim 1 wherein the encoding module includes both radio frequency and gradient field coils.

5. The device of claim 1 wherein elements a., b., c., and d. are incorporated onto a single platform.

6. The device of claim 5 wherein the single platform is a printed circuit board.

7. The device of claim 5 wherein the single platform is a chip.

8. The device of claim 1 wherein the detection module includes at least two magnetoresistive sensors arranged in gradiometer mode.

9. The method of claim 8 wherein the two magnetoresistive sensors are anisotropic magnetoresistive sensors.

10. The device of claim 1, wherein the tube has a size from 1 millimeter to about 100 nanometers in diameter.

11. The device of claim 1 wherein a volume of the fluid sample is in the nanoliter range.

12. A method for assay of a fluidic sample using NMR techniques, including:
   a. providing a fluidic sample, the fluidic sample being pre-polarized;
   b. encoding the fluidic sample by inversion of a polarization of the fluidic sample by adiabatic fast passage with a device; and
   c. detecting changes in magnetization of the fluidic sample with a magnetoresistive sensor is positioned to detect such changes.

13. The method of claim 12 wherein the changes in the magnetization of the fluidic sample are detected as the fluidic sample flows past the magnetoresistive sensor.

14. The method of claim 12 wherein the magnetoresistive sensor is an anisotropic magnetoresistive sensor.

15. The method of claim 12 wherein the changes in the magnetization of the fluidic sample are detected with the fluidic sample in a stationary position at the magnetoresistive sensor.

16. The method of claim 12 further including:
   recording the changes in the magnetization of the fluidic sample.

17. The method of claim 12 wherein the fluidic sample is pre-polarized by passing it through a magnetic field.

18. The method of claim 12 wherein the fluidic sample is pre-polarized by spin-exchange optical pumping or metastability-exchange optical pumping.

19. The method of claim 12 wherein the pre-polarized fluidic sample is encoded so as to enable detection of the changes in at least one property selected from the group consisting of $T_1$ relaxation time, $T_2$ relaxation time, chemical shift (between different nuclei), chemical shift differences (homonuclear), fluid velocity, and diffusion weighting.

20. The method of claim 12 wherein a volume of the fluidic sample is in the nanoliter range.

21. The method of claim 12, further comprising:
   flowing the fluidic sample to the device in a first tube having a size from 1 millimeter to about 100 nanometers in diameter; and
   flowing the fluidic sample from the device to the magnetoresistive sensor in a second tube having a size from 1 millimeter to about 100 nanometers in diameter.

\* \* \* \* \*